(12) United States Patent
Watanabe et al.

(10) Patent No.: US 11,047,852 B2
(45) Date of Patent: Jun. 29, 2021

(54) METHOD FOR DETECTING ANALYTE, DETECTION REAGENT KIT, AND DETECTION REAGENT

(71) Applicant: SYSMEX CORPORATION, Kobe (JP)

(72) Inventors: Toshihiro Watanabe, Kobe (JP); Seiichi Hashida, Tokushima (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 15/216,988

(22) Filed: Jul. 22, 2016

(65) Prior Publication Data

US 2017/0030899 A1 Feb. 2, 2017

(30) Foreign Application Priority Data

Jul. 31, 2015 (JP) .............................. JP2015-152795

(51) Int. Cl.
*G01N 33/543* (2006.01)
*G01N 33/544* (2006.01)

(52) U.S. Cl.
CPC ..... *G01N 33/54306* (2013.01); *G01N 33/544* (2013.01); *G01N 33/54313* (2013.01); *G01N 33/54353* (2013.01); *G01N 2333/76* (2013.01)

(58) Field of Classification Search
CPC ......... G01N 2333/76; G01N 33/54306; G01N 33/54313; G01N 33/54353; G01N 33/544
See application file for complete search history.

(56) References Cited

U.S. PATENT DOCUMENTS

| | | | |
|---|---|---|---|
| 4,782,023 | A | 11/1988 | Anawis et al. |
| 4,891,311 | A | 1/1990 | Anawis et al. |
| 5,236,849 | A | 8/1993 | Ishikawa |
| 2006/0246523 | A1 | 11/2006 | Bieniarz et al. |
| 2011/0129815 | A1 | 6/2011 | Yamagaito et al. |
| 2014/0113315 | A1 | 4/2014 | Brieden et al. |

FOREIGN PATENT DOCUMENTS

| | | |
|---|---|---|
| JP | H08-304397 A | 11/1996 |
| JP | 2011-137747 A | 7/2011 |

OTHER PUBLICATIONS

Rampersand et al., "Novel dPEG® Reagent for Eliminating Aggregation Problems in Protein Complexes," Poster, 2011, retrieved from http://dev2.quantabiodesign.com/references/novel_dpeg_reagent_for_eliminating_aggregation_problems_in_protein_complexes_pep_talk_2011/ on Aug. 2, 2018, posted on Internet Mar. 28, 2011.*
Wang et al., "Sensitive Immunoassay of a Biomarker Tumor Necrosis Factor-α Based on Poly(guanine)-Functionalized Silica Nanoparticle Label," Anal. Chem., 2006, vol. 78, No. 19, pp. 6974-6979.*
Instructions, SM(PEG)8 Crosslinkers retrieved from https://assets.fishersci.com/TFS-Assets/LSG/manuals/MAN0016368_2161766_SM_PEG_n_Crosslinkers_UG.pdf on Aug. 2, 2018.*
Numata, Satoshi et al., "Development of an ultra-sensitive enzyme immunoassay for human insulin autoantibodies", Clinical Biochemistry, 2012, vol. 45, XP 55337505A, pp. 1086-1091.
Hashida, Seiichi et al., "Development of an ultrasensitive enzyme immunoassay for human proadrenomedullin N-terminal 20 peptide and direct measurement of two molecular forms of PAMP in plasma from healthy subjects and patients with cardiovascular disease", Clinical Biochemistry, 2004, vol. 37, XP 55042007A, pp. 14-21.
Umehara, Asako et al., "A novel ultra-sensitive enzyme immunoassay for soluble human insulin receptor ectodomain and its measurement in urine from healthy subjects and patients with diabetes mellitus", Clinical Biochemistry, 2009, vol. 42, XP 26524883A, pp. 1468-1475.
Hashida, Seiichi et al., "Shortening of the window period in diagnosis of HIV-1 infection by simultaneous detection of p24 antigen and antibody IgG to p17 and reverse transcriptase in serum with ultrasensitive enzyme immunoassay", Journal of Virological Methods, 1996, vol. 62, XP 55337494A, pp. 43-53.
Japanese Office Action dated Jan. 22, 2019 in a counterpart Japanese patent application No. 2015-152795.
Chinese Official Communication dated May 13, 2019 in a counterpart Chinese patent application No. 201610616364.1.
Japanese Office Action dated Aug. 20, 2019 in a counterpart Japanese patent application No. 2015-152795.
Communication pursuant to Article 94(3) EPC dated Apr. 20, 2020 in a counterpart European patent application No. 16181817.4.
Chinese Retrial Notice issued on Apr. 30, 2020 in a counterpart Chinese patent application No. 201610616364.1.
Examination Report dated Nov. 24, 2020 in a counterpart Australian patent application No. 2016208414.
Examination Report dated Jul. 8, 2020 in a counterpart Australian patent application No. 2016208414.
Chinese Decision of Reexamination issued on Sep. 30, 2020 in a counterpart Chinese patent application No. 201610616364.1.

* cited by examiner

*Primary Examiner* — Galina M. Yakovleva
(74) *Attorney, Agent, or Firm* — Sughrue Mion, PLLC

(57) ABSTRACT

Disclosed is a method for detecting an analyte in a sample, including the steps of:
(A) forming a first complex comprising:
an analyte;
a first trapping body which specifically binds to the analyte;
a second trapping body which specifically binds to a site of the analyte, the site being different from a site to which the first trapping body specifically binds; and
a third trapping body which specifically binds to the second trapping body;
(B) separating a part comprising the analyte and the first trapping body from the third trapping body;
(C) allowing a fourth trapping body to trap the part to form a second complex; and
(D) detecting the analyte of the second complex,
wherein the second trapping body comprises a binding substance which binds to the analyte, a support, and a linker which links the binding substance and the support with each other.

7 Claims, 7 Drawing Sheets

METHOD FOR DETECTING ANALYTE, DETECTION REAGENT KIT, AND DETECTION REAGENT

CROSS REFERENCE TO RELATED APPLICATIONS

This application claims priority from prior Japanese Patent Application No. 2015-152795, filed on Jul. 31, 2015, entitled "METHOD FOR DETECTING TEST SUBSTANCE, DETECTION REAGENT KIT, AND DETECTION REAGENT", the entire contents of which are incorporated herein by reference.

TECHNICAL FIELD

The present invention relates to a method for detecting an analyte

BACKGROUND

An immune complex transfer enzyme immunoassay is disclosed as a method for detecting an analyte (for example, see JP H01-254868). In the method described in JP H01-254868, an immune complex containing an antigen to be measured and an active ingredient is once formed on a carrier. After washing of the carrier, the immune complex is dissociated from the carrier. The dissociated immune complex is bound to another carrier. After washing of the carrier, the immune complex on the carrier is measured.

The method described in JP H01-254868, however, is sometimes difficult to ensure sufficient sensitivity when a very small amount of the analyte is contained in a specimen.

SUMMARY OF THE INVENTION

The scope of the present invention is defined solely by the appended claims, and is not affected to any degree by the statements within this summary.

A first aspect of the present invention includes a method for detecting an analyte in a sample, comprising the steps of: (A) forming a first complex comprising: an analyte; a first trapping body which specifically binds to the analyte; a second trapping body which specifically binds to a site of the analyte, the site being different from a site to which the first trapping body specifically binds; and a third trapping body which specifically binds to the second trapping body; (B) separating a part comprising the analyte and the first trapping body from the third trapping body; (C) allowing a fourth trapping body to trap the part to form a second complex; and (D) detecting the analyte of the second complex,
wherein the second trapping body comprises a binding substance which binds to the analyte, a support, and a linker which links the binding substance and the support with each other.

A second aspect of the present invention includes a method for detecting an analyte in a sample, comprising the steps of: (A) forming a first complex comprising: an analyte; a first trapping body which specifically binds to the analyte; a second trapping body which specifically binds to a site of the analyte, the site being different from a site to which the first trapping body specifically binds; and a third trapping body which specifically binds to the second trapping body; (B) separating a sandwich complex comprising the analyte, the first trapping body, and the second trapping body from the third trapping body; (C) allowing a fourth trapping body to trap the sandwich complex to form a second complex; and (D) detecting the analyte of the second complex,
wherein the second trapping body comprises a binding substance which binds to the analyte, a support, and a linker which links the binding substance and the support with each other.

A third aspect of the present invention includes a method for detecting an analyte in a sample, comprising the steps of: (A) forming a first complex comprising: an analyte; a first antibody which specifically binds to the analyte by an antigen-antibody reaction; a second antibody which specifically binds to a site of the analyte by an antigen-antibody reaction, the site being different from a site to which the first trapping body specifically binds, wherein the second antibody comprises a dinitrophenyl group and a biotin; and an anti-dinitrophenyl antibody solid phase; (B) separating a sandwich complex comprising the analyte, the first antibody, the second antibody from the anti-dinitrophenyl antibody solid phase; (C) allowing an avidin solid phase or a streptavidin solid phase to trap the sandwich complex to form a second complex; and (D) detecting the analyte of the second complex,
wherein the second antibody comprises a binding substance which binds to the analyte, a support, and a linker which links the binding substance and the support with each other.

DETAILED DESCRIPTION OF THE PREFERRED EMBODIMENTS

1. Method for Detecting Test Substance

Figure 1:
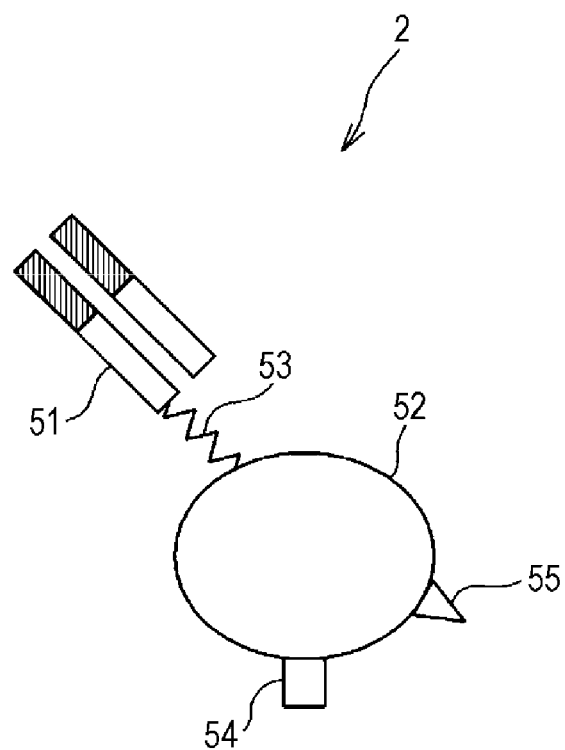
FIG. 1 is a schematic explanatory view of a second trapping body.

The method for detecting an analyte according to the present embodiment includes the steps of: (A) forming a first complex containing an analyte, a first trapping body which specifically binds to the analyte, a second trapping body which specifically binds to a site different from a binding site for the first trapping body in the analyte, and a third trapping body which specifically binds to the second trapping body; (B) separating a part including the first trapping body from the first complex; (C) allowing a fourth trapping body to trap the part including the first trapping body to form a second complex; and (D) detecting the analyte contained in the second complex. The second trapping body contains a binding substance which binds to the analyte, a support, and a linker which links the binding substance and the support with each other. The method for detecting an analyte according to the present embodiment can be carried out, for example, by a method involving use of an antigen-antibody reaction, such as immunoassay. In this case, the first trapping body and the analyte form a complex with use of an antigen-antibody reaction. The second trapping body and the analyte form a complex with use of an antigen-antibody reaction.

An immune complex transfer enzyme immunoassay (hereinafter, referred to also as "ICT-EIA") involves trapping an analyte with two trapping bodies with the analyte being sandwiched therebetween to form an immune complex. The present inventors have found that, in a conventional immune complex transfer enzyme immunoassay, the sensitivity is lowered by dissociation of a part of the immune complex. In the case of a very small amount of the analyte, it is sometimes difficult to ensure sufficient sensitivity. Contrary to this, the method for detecting an analyte according to the present embodiment employs a second trapping body in which a binding substance and a support are linked with each other by a linker. Thus, in the method for detecting an analyte according to the present embodiment, the first trapping body and the second trapping body trap the analyte while sandwiching the analyte to form a sandwich complex. This is considered to suppress the occurrence of steric hindrance when the analyte is trapped by the second trapping body. Therefore, the dissociation of the complex made up of the first trapping body, the analyte and the second trapping body is considered to be suppressed, thereby making it possible to improve the sensitivity in detection of the analyte.

Examples of the analyte include, but are not particularly limited to, an antibody, an antigen, a nucleic acid, a physiologically active substance, a bacterium, a virus, a peptide, and a therapeutic agent (blood drug). An antibody can serve also as an antigen. Examples of the antibody include, but are not particularly limited to, an antibody to an antigen and an antibody to an antibody. Examples of the antigen include, but are not particularly limited to, a nucleic acid, a physiologically active substance, a bacterium, a virus, and a peptide. Examples of the nucleic acid include, but are not particularly limited to, nucleic acids encoding, for example, a disease-causing gene, and a nucleic acid encoding a gene of a bacterium or a virus. Examples of the physiologically active substance include, but are not particularly limited to, a cell growth factor, a differentiation-inducing factor, a cell adhesion factor, an enzyme, a cytokine, a hormone, and a sugar chain.

The first trapping body contains a first binding substance which specifically binds to the analyte. The term "specifically" as used therein means that the binding substance does not substantially bind to any substance other than a specific substance, or does not cause an antigen-antibody reaction with any substance other than a specific substance at a substantially detectable level. The first trapping body preferably further has a detectable labeling substance from the viewpoint of enhancing the ease of detecting the analyte.

Examples of the first binding substance include, but are not particularly limited to, an antibody, an aptamer, an affibody (registered trademark of Affibody AB), a lectin, and a nucleic acid. The concept "antibody" as used herein encompasses also an "antibody fragment," unless otherwise noted. The antibody as the first binding substance functions to specifically bind to the analyte. Examples of the antibody include, but are not particularly limited to, a mouse-derived antibody, a rabbit-derived antibody, a goat-derived antibody, a sheep-derived antibody, a guinea pig-derived antibody, an eel-derived antibody, a shark-derived antibody, a humanized antibody, and a chimeric antibody. The antibody may be either a monoclonal antibody or a polyclonal antibody. Examples of the antibody fragment include, but are not particularly limited to, Fab, Fab', F(ab')$_2$, and a single-chain antibody [scFc]. The aptamer may be either a nucleic acid aptamer or a peptide aptamer. The affibody (registered trademark) is a polypeptide having a specific domain of protein A as a backbone. The affibody functions to specifically bind to the analyte. A lectin is a protein which specifically binds to a sugar chain as the analyte. The nucleic acid is a nucleic acid which specifically binds to a nucleic acid as the analyte. Examples of the nucleic acid include, but are not particularly limited to, a DNA, an RNA, a peptide nucleic acid (PNA), and a bridged nucleic acid (BNA). Among these binding substances, an antibody is preferred.

Examples of the labeling substance include, but are not particularly limited to, an enzyme, a fluorescent substance and a radioactive substance. Examples of the enzyme include, but are not particularly limited to, β-galactosidase, peroxidase, alkaline phosphatase and luciferase. Examples of the fluorescent substance include, but are not particularly limited to, fluorescein, fluorescein isothiocyanate, coumarin, rhodamine, fluorescein, Cy3, Cy5, Hoechst 33342, 4',6-diamino-2-phenylindole (DAPI), propidium iodide (PI), and pigments of the series Alexa Fluor (registered trademark of Molecular Probes). Examples of the radioactive substance include, but are not particularly limited to, $^{32}$P and $^{35}$S. The labeling substance is preferably an enzyme, more preferably β-galactosidase and alkaline phosphatase.

The second trapping body specifically binds to a site different from a binding site for the first trapping body in the analyte. Thus, the second trapping body does not compete with the first trapping body at the time of binding to the analyte. The second trapping body contains a second binding substance which binds to the analyte, a support and a linker. The linker links the second binding substance and the support with each other. The support has a first reactive group and a second reactive group.

The second binding substance is a substance which specifically binds to a site different from a binding site for the first trapping body in the analyte. Examples of the second binding substance include, but are not particularly limited to, an antibody, an aptamer, an affibody (registered trademark of Affibody AB), a lectin, and a nucleic acid. The antibody as the second binding substance functions to specifically bind to the analyte. Examples of the antibody include, but are not particularly limited to, a mouse-derived antibody, a rabbit-derived antibody, a goat-derived antibody, a sheep-derived antibody, a guinea pig-derived antibody, an eel-derived antibody, a shark-derived antibody, a humanized antibody, and a chimeric antibody.

Examples of the support include, but are not particularly limited to, a polypeptide, dextran and casein. The polypeptide is a polypeptide which has no binding site for the first trapping body. The polypeptide varies depending on the kind of the analyte. Examples of the polypeptide include, but are not particularly limited to, albumins such as bovine serum albumin and human serum albumin.

Any substance may be used as the first reactive group without particular limitation so long as the substance can bind to the third trapping body. Examples of the first reactive group include a dinitrophenyl (DNP) group, biotin, an antibody, an antigen, avidin, and streptavidin.

Any substance may be used as the second reactive group so long as the substance can bind to the fourth trapping body. Examples of the second reactive group include a DNP group, biotin, an antibody, an antigen, avidin, and streptavidin.

As used herein, the term "linker" refers to a molecule which links the second binding substance and the support with each other. Examples of the linker include, but are not particularly limited to, a polymer chain optionally having at least one selected from the group consisting of a substituent, an oxygen atom, a sulfur atom and a nitrogen atom. Examples of the polymer chain include, but are not particularly limited to, a polyalkylene glycol chain having an oxyalkylene group having 2 to 6 carbon atoms, and a polymer chain represented by Formula (I):

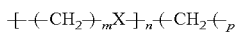 [Formula I]

wherein X represents a nitrogen atom, an oxygen atom, a sulfur atom, an alkylene group having 1 to 4 carbon atoms, an —NHCO— group, an optionally substituted aryl group having 6 to 12 carbon atoms, or an optionally substituted cycloalkyl group having 3 to 8 carbon atoms; and m, n and p are mutually independent, and each represent positive integers of 2 or more. The polymer chain represented by Formula (I) has one terminal end to which the second binding substance is linked. The support is linked to the other terminal end of the polymer chain. The polymer chain of Formula (I) may be bound to the second binding substance or the support via a functional group for binding to the binding substance or the support.

In the polyalkylene glycol chain, the number of carbon atoms possessed by the oxyalkylene group is 2 to 6, preferably 2 to 4. In the polyalkylene glycol chain, the average addition molar number of the oxyalkylene groups is 2 to 100, preferably 2 to 20. The mass average molecular weight of the polyalkylene glycol chain is preferably 116 to 12000, more preferably 116 to 2000. Examples of the oxyalkylene group having 2 to 6 carbon atoms include, but are not particularly limited to, an oxyethylene group and an oxypropylene group. Examples of the polyalkylene glycol chain include, but are not particularly limited to, polyethylene glycol and polypropylene glycol. The polyalkylene glycol chain may be any of a homopolymer, an alternating copolymer, a block copolymer, and a random copolymer. The "mass average molecular weight" is a value obtained by gel filtration chromatography.

In formula (I), X represents a nitrogen atom, an oxygen atom, a sulfur atom, an alkylene group having 1 to 4 carbon atoms, an —NHCO— group, an optionally substituted aryl group having 6 to 12 carbon atoms, or an optionally substituted cycloalkyl group having 3 to 8 carbon atoms. The number of carbon atoms possessed by the aryl group is 6 to 12, preferably 6 to 8, more preferably 6 to 7. Examples of the substituent which may be possessed by the aryl group include, but are not particularly limited to, a methyl group, an oxo group, a carboxyl group, and an amino group. Examples of the aryl group include, but are not particularly limited to, a phenyl group and a tolyl group. The number of carbon atoms possessed by the cycloalkyl group is 3 to 8, preferably 4 to 6. The substituent which may be possessed by the cycloalkyl group is similar to the substituent which may be possessed by the aryl group. Examples of the cycloalkyl group include, but are not particularly limited to, a cyclopropyl group, a cyclobutyl group, a cyclopentyl group, and a cyclohexyl group.

Among these linkers, preferred is a polyalkylene glycol chain having an oxyalkylene group having 2 to 6 carbon atoms, and more preferred is a polyalkylene glycol chain having an oxyalkylene group having 2 to 6 carbon atoms whose average addition molar number is 2 to 100, from the viewpoint of suppressing, for example, the dissociation of the analyte at the time of forming a sandwich complex. Among the polyalkylene glycol chains, preferred is a polyethylene glycol chain, and more preferred is a polyethylene glycol chain having an oxyethylene group whose average addition molar number is 2 to 100, from the viewpoint of suppressing, for example, the dissociation of the analyte at the time of forming a sandwich complex with more certainty.

The third trapping body specifically binds to the second trapping body. The third trapping body preferably contains a third binding substance which binds to the second trapping body and a solid phase which retains the binding substance. The third binding substance in the third trapping body binds to a site different from a binding site for the analyte in the second trapping body. Examples of the third binding substance in the third trapping body include, but are not particularly limited to, an antibody, an aptamer, an affibody (registered trademark of Affibody AB), a lectin, a nucleic acid, biotin, avidin, and streptavidin. The antibody as the third binding substance functions to specifically bind to the analyte. Examples of the antibody include, but are not particularly limited to, a mouse-derived antibody, a rabbit-derived antibody, a goat-derived antibody, a sheep-derived antibody, a guinea pig-derived antibody, an eel-derived antibody, a shark-derived antibody, a humanized antibody, and a chimeric antibody. Examples of the solid phase include, but are not particularly limited to, a particle and a plate. Examples of the particle include, but are not particularly limited to, a magnetic particle and a latex particle. Examples of the plate include, but are not particularly limited to, a polystyrene plate. Examples of a combination of the first reactive group in the second trapping body and the third binding substance in the third trapping body include, but are not particularly limited to, a combination of a hapten and an anti-hapten antibody and a combination of a different antigen and a different antibody. Examples of the combination of a hapten and an anti-hapten antibody include, but are not particularly limited to, DNP-anti-DNP antibody and biotin-anti-biotin antibody.

The fourth trapping body traps a part including the first trapping body. The phrase "part including the first trapping body" refers to a portion enough to ensure the correlation between the amount of the first trapping body and the amount of the analyte. The part including the first trapping body is preferably a portion of the first complex except the third trapping body. Examples of the part including the first trapping body include a complex of the first trapping body and the analyte, and a complex of the first trapping body, the analyte and the second trapping body. The fourth trapping body preferably contains a fourth binding substance which binds to the part including the first trapping body, and a solid phase. Examples of the fourth binding substance includes an antibody, an antibody fragment, an aptamer, an affibody (registered trademark of Affibody AB), a lectin, a nucleic acid, biotin, avidin, streptavidin, and a substance which binds to the reactive group possessed by the support in the second trapping body. The solid phase fixes and retains the fourth binding substance. Examples of the solid phase in the fourth trapping body include those which are similar to the solid phases in the third trapping body. Examples of the combination of the second reactive group in the second trapping body and the fourth binding substance in the fourth trapping body include, but are not particularly limited to, a combination of a hapten and an anti-hapten antibody and a combination of a different antigen and a different antibody. Examples of the combination of a hapten and an anti-hapten antibody include, but are not particularly limited to, DNP-anti-DNP antibody and biotin-anti-biotin antibody. The combination of the second reactive group and the fourth trapping body is different from the combination of the first reactive group and the third trapping body.

FIG. 1 shows one example of the second trapping body. A second trapping body 2 as shown in FIG. 1 contains Fab' as a second binding substance 51, a support 52 and a linker 53. The second binding substance 51 and the support 52 are linked with each other by the linker 53. The support 52 has, on its surface, a first reactive group 54 and a second reactive group 55. The first reactive group 54 is a portion capable of binding to or being detached from a third trapping body. The second reactive group 55 is a portion capable of binding to a fourth trapping body.

The third binding substance in the third trapping body may be a substance which binds to the first reactive group 54 possessed by the support 52 in the second trapping body 2 shown in FIG. 1. The substance which binds to the first reactive group 54 shown in FIG. 1 can appropriately be selected depending on the kind of the first reactive group 54 in FIG. 1. Examples of the combination of the first reactive group 54 in FIG. 1 and the third binding substance in the third trapping body include, but are not particularly limited to, a combination of a DNP group and an anti-DNP antibody, a combination of a trinitrophenyl (TNP) group and an anti-TNP antibody, and a combination of biotin and avidin.

The substance which binds to the second reactive group 55 in FIG. 1 can appropriately be selected depending on the kind of the second reactive group 55 in FIG. 1. Examples of the combination of the second reactive group 55 and the fourth binding substance in the fourth trapping body include, but are not particularly limited to, a combination of a DNP group and an anti-DNP antibody, a combination of a TNP group and an anti-TNP antibody, a combination of biotin and avidin, and a combination of biotin and streptavidin.

Figure 2:
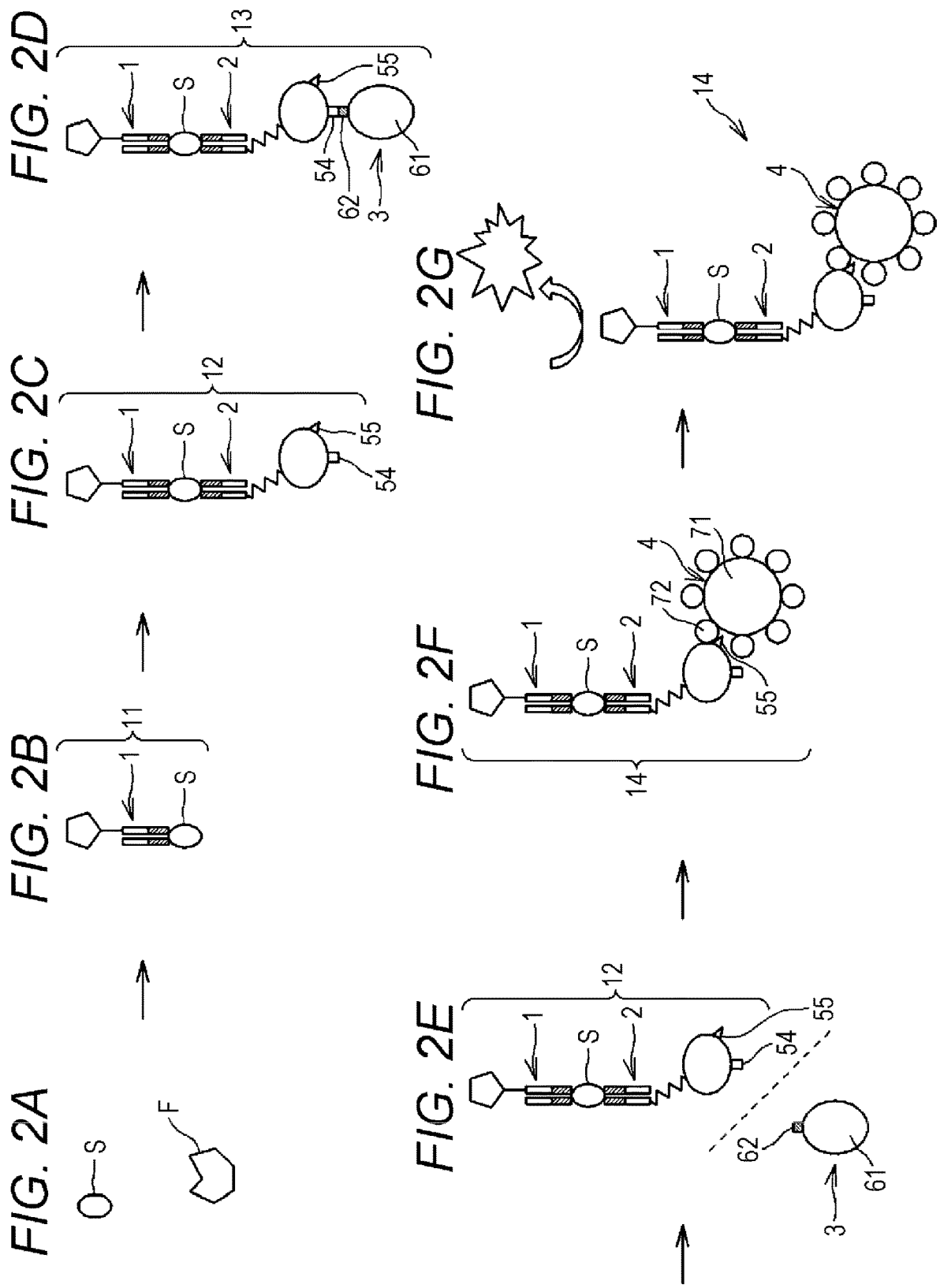
FIGS. 2A, 2B, 2C, 2D, 2E, 2F and 2G are process charts of example procedures of a method for detecting an analyte.

Next, explained are example procedures of the method for detecting an analyte according to the present embodiment. FIGS. 2A, 2B, 2C, 2D, 2E, 2F and 2G show example procedures of the method for detecting an analyte according to the present embodiment. In FIGS. 2A-2G, an explanation is given about an example case of detection of an analyte S in a specimen containing the analyte S and a contaminant F as shown in FIG. 2A. In FIGS. 2A-2G, the kinds of a first trapping body 1, a second trapping body 2, a third trapping body 3 and the like are not particularly limited. The term "contaminant" refers to a substance other than the analyte. In FIGS. 2A-2G, the first trapping body 1, the second trapping body 2 and the third trapping body 3 are brought in contact with the analyte S in this order to form a first complex 13. The order of mixing the analyte S, the first trapping body 1, the second trapping body 2, and the third trapping body 3, however, is not particularly limited.

In the step (A), the first complex 13 containing the analyte S, the first trapping body 1, the second trapping body 2, and the third trapping body 3 is formed. Specifically, the first trapping body 1 is firstly contacted with a specimen containing the analyte S and the contaminant F, as shown in FIGS. 2A and 2B. This allows formation of a complex 11 containing the first trapping body 1 and the analyte S. Then, as shown in FIG. 2C, the complex 11 and the second trapping body 2 are contacted with each other. This allows formation of a sandwich complex 12. The sandwich complex 12 is a complex bound to the first trapping body 1 and the second trapping body 2 in such a manner that the analyte S is sandwiched between the first trapping body 1 and the second trapping body 2. Then, the sandwich complex 12 and the third trapping body 3 are contacted with each other. This allows formation of the first complex 13, as shown in FIG. 2D. The first complex 13 contains the first trapping body 1, the analyte S, the second trapping body 2, and the third trapping body 3. In FIG. 2D, the third trapping body 3 contains a solid phase 61 and a third binding substance 62 fixed onto the solid phase 61. In the formation of the first complex 13, as shown in FIG. 2D, the third binding substance 62 in the third trapping body 3 binds to the first reactive group 54 in the second trapping body 2.

The first complex 13 can be formed, for example, with use of an antigen-antibody reaction. The antigen-antibody reaction is preferably utilized for the formation of the first complex 13, from the viewpoint of enhancing the specificity to the analyte S and improving the sensitivity. In this case, the first trapping body 1 preferably contains a substance which specifically binds to the analyte S through an antigen-antibody reaction. The second trapping body 2 preferably contains a substance which specifically binds to the analyte S through an antigen-antibody reaction as the second binding substance. When the analyte S is an antigen, there can be used an antibody which specifically binds to an antigen, an antibody fragment obtained by fragmentation of this antibody, and the like. On the other hand, when the analyte S is an antibody, there can be used an antigen for this antibody, an antibody which specifically binds to the antibody, and the like.

The first complex 13 can be formed under conditions in accordance with the kinds of the analyte S, the first trapping body 1, the second trapping body 2, and the third trapping body 3. The first complex 13 can be formed in a solution. Any solution may be used so long as it is suitable for the binding of the first trapping body 1, the analyte S, the second trapping body 2, and the third trapping body 3. Any temperature for forming the first complex 13 may be employed so long as it is suitable for the binding of the first trapping body 1, the analyte S, the second trapping body 2, and the third trapping body 3. Any time for forming the first complex 13 may be employed so long as it is enough for the binding of the first trapping body 1, the analyte S, the second trapping body 2, and the third trapping body 3.

From the viewpoint of improving the sensitivity, a step of removing the first trapping body 1 in a free state and the second trapping body 2 in a free state (hereinafter referred to also as a "first removal step") can further be carried out between the step (A) and the step (B) which will be described below. In the first removal step, washing with a buffer, for example, can be performed. Examples of the buffer include, but are not particularly limited to, phosphate buffered saline, a sodium phosphate buffer, and a tris-hydrochloric acid buffer. Any pH of the buffer may be employed so long as the pH falls within such a range as to ensure stable retention of the first complex 13. In the first removal step, the contaminant F in a free state is also removed.

In the step (B), a part including the first trapping body 1 is separated from the first complex 13, as shown in FIG. 2E. The part including the first trapping body 1 is preferably the complex 11 and the sandwich complex 12, more preferably the sandwich complex 12, from the viewpoint of ensuring ease of separation and sufficient quantitative capability. In FIG. 2E, the sandwich complex 12 is separated from the first complex 13, as the part including the first trapping body 1. However, the part including the first trapping body 1 may be a portion other than the sandwich complex 12. Separation can be performed, for example, by a separation method in accordance with the type of a bond included in the first complex 13. Examples of the bond included in the first complex 13 include a bond between the first trapping body 1 and the second trapping body 2, a bond between the second trapping body 2 and the third trapping body 3, a bond included in the complex 11, and a bond included in the sandwich complex 12. Specific examples of the bond included in the first complex include, but are not particularly limited to, a bond via a disulfide bond and a bond via a DNP group. Examples of the bond via a disulfide bond include, but are not particularly limited to, a bond between an antigen and an antibody via a disulfide bond and a bond between biotin and avidin or streptavidin. Examples of the bond via a DNP group include, but are not limited to, a bond between DNP and an anti-DNP antibody. For separation, there can be used a separation reagent for separating at least the third trapping body 3 from the first complex 13 without breaking the first trapping body 1. When the first complex 13 has a disulfide bond in its portion except the first trapping body 1, a disulfide bond breaking reagent can be used as the separation reagent. Examples of the disulfide bond breaking reagent include, but are not particularly limited to, 2-mercaptoethanol and dithiothreitol. When the first complex 13 has a bond via a DNP group in its portion except the first trapping body 1, a dinitrophenyl amino acid can be used as the separation reagent. Examples of the dinitrophenyl amino acid include, but are not particularly limited to, dinitrophenyl lysine.

After the first removal step, the first trapping body 1 in a free state and the second trapping body 2 in a free state remain in some cases. Thus, a step of removing the first trapping body 1 in a free state and the second trapping body 2 in a free state can further be carried out between the step (B) and the step (C) which will be described below, from the viewpoint of improving the sensitivity.

In the step (C), the part including the first trapping body 1 is trapped by the fourth trapping body 4 as shown in FIG. 2F. This allows formation of a second complex 14. In FIG. 2F, the fourth trapping body 4 contains a solid phase 71 and a fourth binding substance 72 fixed onto the solid phase 71. In the formation of the second complex 14, the fourth binding substance 72 in the fourth trapping body 4 binds to the second reactive group 55 in the second trapping body 2, as shown in FIG. 2F. The second complex 14 can be formed by a technique similar to that for forming the first complex 13 in the step (A).

A step of removing the fourth trapping body in a free state can further be performed between the step (C) and the step (D) which will be described below, from the viewpoint of improving the sensitivity.

In the step (D), the analyte S contained in the second complex 14 is detected as shown in FIG. 2G. The analyte can be detected through detection of a signal based on a labeling substance contained in the first trapping body 1 when the first trapping body 1 contains the labeling substance. Examples of the signal include, but are not particularly limited to, luminescence, fluorescence, color development and radiation. The signal is preferably luminescence, fluorescence and color development because of ease of detection. The signal based on the labeling substance can be detected by a detection method according to the kind of the labeling substance. When the labeling substance is an enzyme, the signal can be detected, for example, by measuring the amount of a product generated from an enzyme substrate through an enzyme reaction. The enzyme substrate is preferably a color-developing substrate and a chemiluminescent substrate because of ease of measuring the amount of the product. The enzyme substrate can appropriately be selected according to the kind of the enzyme. When the labeling substance is a fluorescent substance, the signal can be detected, for example, by measuring the intensity of fluorescence based on the fluorescent substance or the shift of the fluorescence wavelength. When the labeling substance is a radioactive substance, the signal can be detected, for example, by measuring the amount of radiation generated from the radioactive substance.

2. Reagent Kit for Detecting Test Substance

A detection reagent kit according to the present embodiment includes: a first trapping body capable of binding to an analyte; a second trapping body capable of binding to a site different from a binding site for the first trapping body in the analyte; and a third trapping body capable of binding to the second trapping body, and the second trapping body contains a binding substance which binds to the analyte (the above-mentioned second binding substance), a support, and a linker which links the binding substance and the support with each other. The first trapping body, the second trapping body, the third trapping body, the fourth trapping body, the binding substance (the above-mentioned second binding substance), the support and the linker are similar to those used in the above-mentioned method for detecting an analyte. The first trapping body, the second trapping body, the third trapping body and the fourth trapping body can be provided in a state where they are dissolved in an appropriate solvent. The first trapping body, the second trapping body and the third trapping body, and the fourth trapping body are preferably accommodated in separate containers, from the viewpoint of suppressing non-specific detection of a contaminant. The first trapping body, the second trapping body, the third trapping body and the fourth trapping body may be accommodated in separate containers. Two or more of the first trapping body, the second trapping body and the third trapping body may be accommodated in the same container.

The detection reagent kit according to the present embodiment may further include an aid. Examples of the aid include, but are not particularly limited to, a preservative or a stabilizer for stably maintaining the first trapping body, the second trapping body, the third trapping body and the fourth trapping body; a reagent for forming the first complex containing the first trapping body, the second trapping body and the third trapping body; a separation reagent; and a reagent for forming the second complex containing the fourth trapping body and the part including the first trapping body. Examples of the aid include a buffer.

When the first trapping body has a labeling substance, the detection reagent kit according to the present embodiment may further include a reagent necessary for the detection of a signal based on the labeling substance. The reagent necessary for the signal detection can appropriately be selected according to the kind of the labeling substance. Examples of the reagent necessary for the signal detection include, but are not particularly limited to, an enzyme substrate and a color developing agent.

Figure 3:
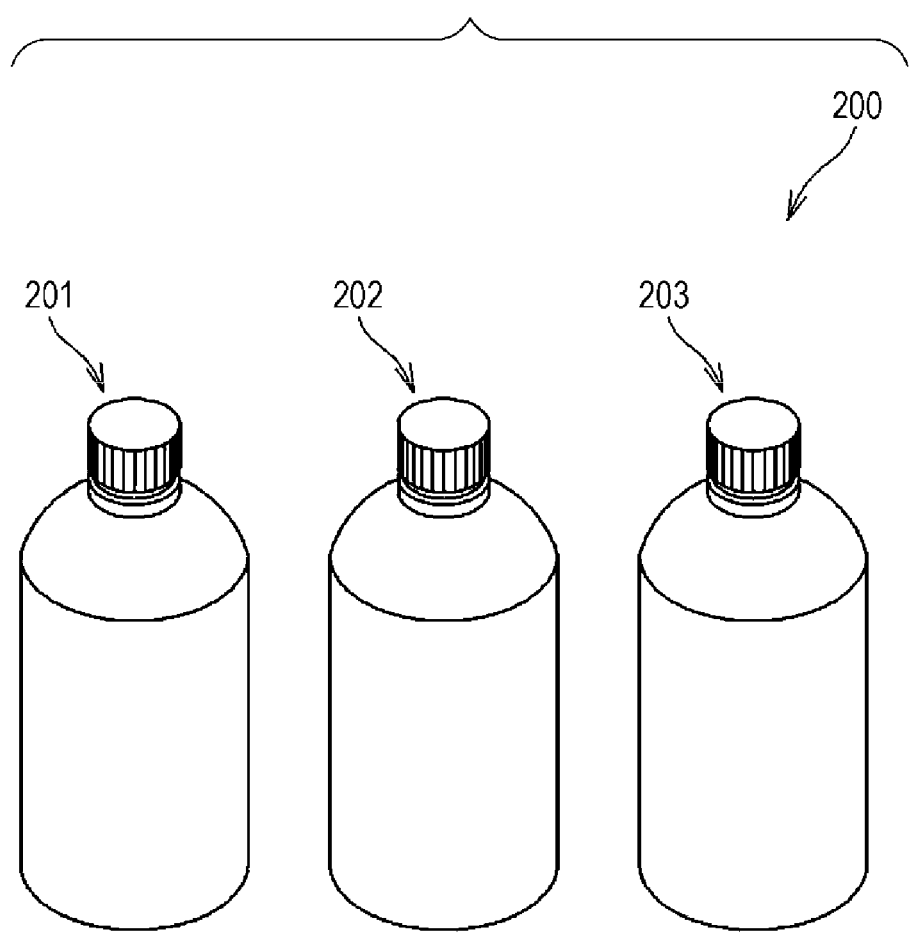
FIG. 3 is a configuration diagram of a detection reagent kit.

One example of the detection reagent kit according to the present embodiment is a detection reagent kit 200 as shown in FIG. 3, without particular limitation. The reagent kit 200 shown in FIG. 3 includes a first reagent container 201, a second reagent container 202 and a third reagent container 203. The first reagent container 201 accommodates a first trapping body capable of binding to an analyte. The second reagent container 202 accommodates a second trapping body capable of binding to a site different from a binding site for the first trapping body in the analyte. The third reagent container 203 accommodates a third trapping body capable of binding to the second trapping body. The detection reagent kit according to the present embodiment may further include a package leaflet. The package leaflet may include, for example, a description of operation procedures for carrying out the above-mentioned method for detecting an analyte using the detection reagent kit according to the present embodiment.

3. Reagent for Detecting Test Substance

A reagent for detecting an analyte according to the present embodiment is a reagent for detecting an analyte for use in the above-mentioned method for detecting an analyte. The reagent for detecting an analyte according to the present embodiment contains a second trapping body capable of binding to the analyte. The second trapping body contains a binding substance which binds to the analyte (the above-mentioned second binding substance), a support, and a linker which links the binding substance (the above-mentioned second binding substance) and the support with each other. The second trapping body, the binding substance (the above-mentioned second binding substance), the support and the linker are similar to those used in the above-mentioned method for detecting an analyte.

The detection reagent according to the present embodiment may further contain an aid. Examples of the aid include, but are not particularly limited to, a preservative or a stabilizer for stably maintaining the second trapping body. Examples of the aid include a buffer.

EXAMPLES

Hereinafter, the meanings of abbreviations are as follows.

Abbreviations

BSA: bovine serum albumin
DNP: 2,4-dinitrophenyl group
Bio: biotinyl group
EMCS: N-(6-maleimidecaprolyloxy) succinimide
SH: thiol group
mal: maleimide group
BSA-Bio-DNP: BSA modified with biotin and DNP
$(PEG)_8$-BSA-Bio-DNP: BSA-Bio-DNP to which a PEG linker is added
TNFα: tumor necrosis factor α
4-MUG: 4-methylumbelliferyl-β-D-galactopyranoside
DMF: N,N-dimethylformamide
PEG: polyethylene glycol chain
(PEG)n: polyethylene glycol chain having an addition molar number of oxyethylene groups of n
Gal: β-galactosidase Example 1

(1) Formation of Sandwich Complex

In order that the amounts of a trapping antibody, a detection antibody and TNFα (manufactured by R&D systems, Inc., trade name: Quantikine Kitstandard) as an analyte which are shown in Table 1 were as shown in Table 1, 100 μL of an antibody solution containing the trapping antibody and the detection antibody and 100 μL of an analyte-containing solution were mixed in a tube. Buffer A (0.4 M sodium chloride, 0.1 mass % BSA and 0.1 M sodium phosphate buffer (pH 7.0)) was used as a solvent for the antibody solution and the analyte-containing solution. The trapping antibody shown in Table 1 was prepared as follows. In accordance with a conventional technique, anti-TNFα mouse IgG obtained from clone name: Mab1 manufactured by Biolegend, Inc. was fragmented with pepsin, thereby obtaining an $F(ab')_2$ fragment. The resultant $F(ab')_2$ fragment was reduced, thereby obtaining Fab'-SH. BSA-Bio-DNP and a linker (manufactured by Life Technologies, trade name: SM(PEG)8) were reacted with each other, thereby obtaining $(PEG)_8$-BSA-Bio-DNP. Fab'-SH and $(PEG)_8$-BSA-Bio-DNP were reacted with each other, thereby obtaining a trapping antibody.

The detection antibody shown in Table 1 was prepared as follows. In accordance with a conventional technique, an anti-mouse IgG antibody obtained from clone name: 28401 manufactured by R&D systems, Inc. was fragmented with pepsin, thereby obtaining an $F(ab')_2$ fragment. The resultant $F(ab')_2$ fragment was reduced, thereby obtaining Fab'-SH. EMCS was reacted with Gal, thereby obtaining Gal-mal. Fab'-SH and Gal-mal were reacted with each other, thereby obtaining a detection antibody.

TABLE 1

|  |  | Amount used |
|---|---|---|
| Trapping antibody | Fab'-$(PEG)_8$-BSA-Bio-DNP | 300 fmol |
| Detection antibody | Fab'-Gal | 30 fmol |
| Test substance | TNFα | 0 or 10 pg |

Two hundred (200) μL of the resultant mixture was incubated at 4° C. for 12 hours, thereby forming a sandwich complex.

(2) Trapping of Sandwich Complex

One anti-DNP antibody solid phase (manufactured by Immunochemical, trade name: Immuno bead 6.35φ, solid phase having an anti-DNP antibody immobilized thereon) was added to the tube containing the sandwich complex obtained in Example 1, item (1). The resultant mixture was incubated at 25° C. for 30 minutes, thereby trapping the sandwich complex on the anti-DNP solid phase. Then, the mixture in the tube was washed twice with 2 mL of a washing liquid (0.1 M sodium chloride, 0.1 mass % BSA and 0.1 M sodium phosphate buffer (pH 7.0)). Thereafter, the anti-DNP antibody solid phase was recovered.

(3) Recovery of Supernatant and Anti-DNP Solid Phase

The complex recovered in Example 1, item (2) was added to 150 μL of a 2 mM DNP solution. The resultant mixture was incubated at 25° C. for 30 minutes, thereby breaking a bond between the anti-DNP solid phase and the sandwich complex. A supernatant of the resultant product was transferred to another tube. The remaining anti-DNP antibody solid phase was washed twice with 2 mL of buffer B (0.1 M sodium chloride, 0.1 mass % BSA and 0.1 M sodium phosphate buffer (pH 7.0)).

(4) Trapping of Sandwich Complex

To the supernatant recovered in Example 1, item (3), one streptavidin solid phase (manufactured by Immunochemical, trade name: Immuno bead 6.35φ, solid phase having streptavidin immobilized thereon) was added. The resultant mixture was incubated at 25° C. for 30 minutes, thereby trapping the sandwich complex on the streptavidin solid phase. Then, the mixture in the tube was washed three times with 2 mL of buffer B (0.1 M sodium chloride, 0.1 mass % BSA and 0.1 M sodium phosphate buffer (pH 7.0)), thereby recovering the streptavidin solid phase.

(5) Measurement of Fluorescence Intensity

The anti-DNP antibody solid phase recovered in Example 1, item (2) and 200 μL of an aqueous solution of 0.2 mM 4-MUG were added to 200 μL of buffer B (0.1 M sodium chloride, 0.1 mass % BSA and 0.1 M sodium phosphate buffer (pH 7.0)) in a new tube, thereby obtaining a reaction solution. The resultant reaction solution was incubated at 30° C. for 2 hours, thereby obtaining a reaction product. Thereafter, the fluorescence intensity (hereinafter referred to as "fluorescence intensity A1") of the reaction product in the tube was measured at an excitation wavelength: 360 nm and a fluorescence wavelength: 450 nm. Fluorescence intensity A2 was calculated by subtracting from the fluorescence intensity A1 value the fluorescence intensity value when the aqueous solution of 0.2 mM 4-MUG alone was added. The average value (hereinafter referred to as "fluorescence intensity A") of fluorescence intensity A2 was calculated based on the results of the three measurements.

The streptavidin solid phase recovered in Example 1, item (4) and 200 μL of an aqueous solution of 0.2 mM 4-MUG were added to 200 μL of buffer B (0.1 M sodium chloride, 0.1 mass % BSA and 0.1 M sodium phosphate buffer (pH 7.0)) in a new tube, thereby obtaining a reaction solution. The resultant reaction solution was incubated at 30° C. for 20 hours, thereby obtaining a reaction product. Thereafter, the fluorescence intensity (hereinafter referred to as "fluorescence intensity B1") of the reaction product in the tube was measured at an excitation wavelength: 360 nm and a fluorescence wavelength: 450 nm. Fluorescence intensity B2 was calculated by subtracting from the fluorescence intensity B1 value the fluorescence intensity value when the aqueous solution of 0.2 mM 4-MUG alone was added. The average value (hereinafter referred to as "fluorescence intensity B") of fluorescence intensity B2 was calculated based on the results of the three measurements.

The anti-DNP antibody solid phase recovered in Example 1, item (3) and 200 μL of an aqueous solution of 0.2 mM 4-MUG were added to 200 μL of buffer B (0.1 M sodium chloride, 0.1 mass % BSA and 0.1 M sodium phosphate buffer (pH 7.0)) in a new tube, thereby obtaining a reaction solution. The resultant reaction solution was incubated at 30° C. for 2 hours, thereby obtaining a reaction product. Thereafter, the fluorescence intensity (hereinafter referred to as "fluorescence intensity C1") of the reaction product in the tube was measured at an excitation wavelength: 360 nm and a fluorescence wavelength: 450 nm. Fluorescence intensity C2 was calculated by subtracting from the fluorescence intensity C1 value the value when the aqueous solution of 0.2 mM 4-MUG alone was added. The average value (hereinafter referred to as "fluorescence intensity C") of fluorescence intensity C2 was calculated based on the results of the three measurements.

Using fluorescence intensities A, B and C when the weight of the analyte was 10 pg, in accordance with Formula (II):

[Mathematical Formula 1]

$$[\text{Complex retention rate}] = [1 - (1 - \text{fluorescence intensity } C / \text{incubation time } H / (\text{fluorescence intensity } A - \text{fluorescence intensity } B))] \times 100, \quad (II)$$

the complex retention rate was calculated. In Formula (II), the phrase "incubation time H" refers to the time for incubation of the reaction solution.

Comparative Example 1

Except that Fab'-BSA-Bio-DNP was used as the trapping antibody, operations similar to those of Example 1 were performed to calculate the complex retention rate. The trapping antibody was prepared as follows. In accordance with a conventional technique, the anti-TNFα mouse IgG obtained from clone name: Mab1 manufactured by Biolegend, Inc. was fragmented with pepsin, thereby obtaining an $F(ab')_2$ fragment. The resultant $F(ab')_2$ fragment was reduced, thereby obtaining Fab'-SH. BSA-Bio-DNP and EMCS were reacted with each other, thereby obtaining BSA-Bio-DNP-mal. Fab'-SH and BSA-Bio-DNP-mal were reacted with each other, thereby obtaining a trapping antibody.

(Results)

Figure 4:
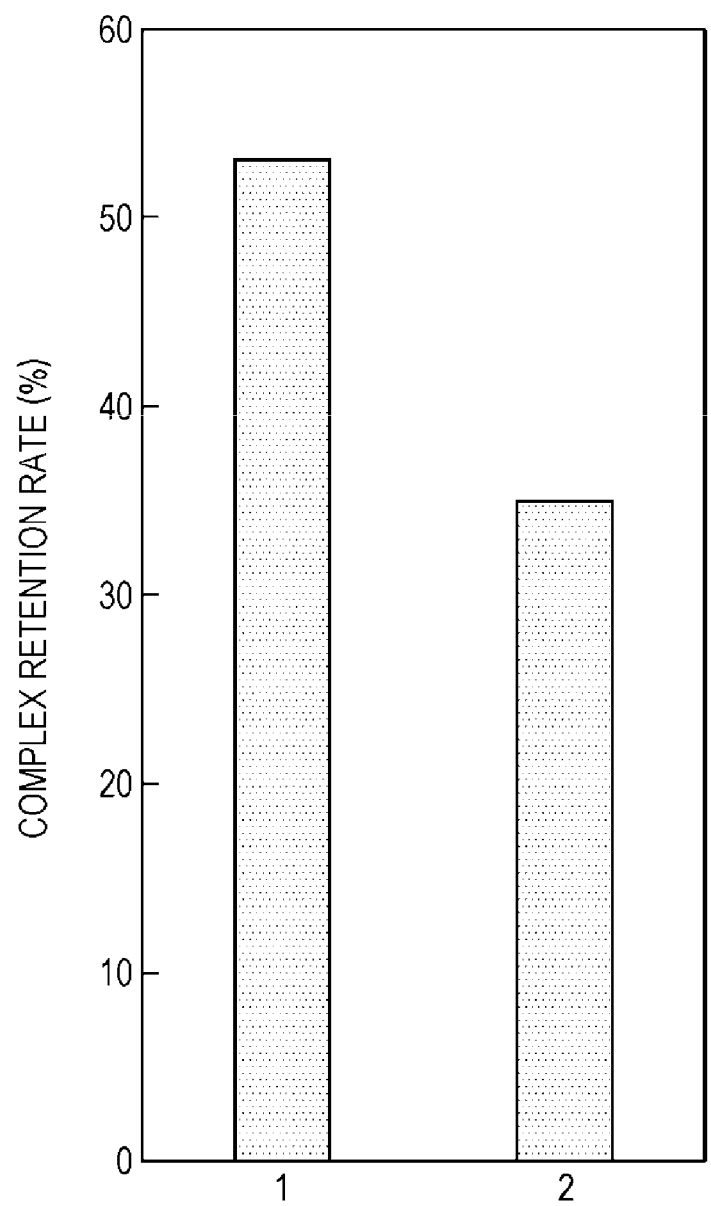
FIG. 4 is a graph showing results of examination of a complex retention rate in Example 1 and Comparative Example 1.

FIG. 4 shows results of Example 1 and Comparative Example 1. In FIG. 4, Lane 1 represents a complex retention rate in Example 1, and Lane 2 represents a complex retention rate in Comparative Example 1.

From the results shown in FIG. 4, it was found that the complex retention rate in Example 1 exceeded 50%. On the other hand, it was found that the complex retention rate in Comparative Example 1 was about 35%. From these results, it was found that the use of a trapping antibody containing a linker can improve the complex retention rate.

Example 2

Operations similar to those of Example 1, items (1) to (4) were performed to recover the streptavidin solid phase. Then, the recovered streptavidin solid phase and 200 μL of an aqueous solution of 0.2 mM 4-MUG were added to 200 μL of buffer B (0.1 M sodium chloride, 0.1 mass % BSA and 0.1 M sodium phosphate buffer (pH 7.0)) in a new tube, thereby obtaining a reaction solution. The resultant reaction solution was incubated at 30° C. for 20 hours, thereby obtaining a reaction product. Thereafter, the fluorescence intensity B1 of the reaction product in the tube was measured at an excitation wavelength: 360 nm and a fluorescence wavelength: 450 nm. Fluorescence intensity B2 was calculated by subtracting from the fluorescence intensity B1 value the fluorescence intensity value when the aqueous solution of 0.2 mM 4-MUG alone was added. Fluorescence intensity B was calculated as the average value of fluorescence intensity B2 based on the results of the three measurements.

Using fluorescence intensity B in the presence of the analyte and fluorescence intensity B in the absence of the analyte, in accordance with Formula (III):

[Mathematical Formula 2]

$$[S/N \text{ ratio}] = [\text{fluorescence intensity in the presence of the analyte}] - [\text{fluorescence intensity in the absence of the analyte}] / [\text{fluorescence intensity in the absence of the analyte}], \quad (III)$$

the S/N ratio in ICT-EIA was calculated. "Fluorescence intensity B in the presence of the analyte" was used as the "fluorescence intensity in the presence of the analyte." "Fluorescence intensity B in the absence of the analyte" was used as the "fluorescence intensity in the absence of the analyte."

Comparative Example 2

Except that Fab'-BSA-Bio-DNP was used as the trapping antibody, operations similar to those of Example 2 were performed to calculate the S/N ratio in ICT-EIA.

Comparative Example 3

(1) Formation of Sandwich Complex

Operations similar to those of Example 1, item (1) were performed to form a sandwich complex.

(2) Trapping of Sandwich Complex

Operations similar to those of Example 1, item (2) were performed to recover the anti-DNP antibody solid phase.

(3) Measurement of Fluorescence Intensity

The anti-DNP antibody solid phase recovered in Comparative Example 3, item (2) and 200 μL of an aqueous solution of 0.2 mM 4-MUG were added to 200 μL of buffer B (0.1 M sodium chloride, 0.1 mass % BSA and 0.1 M sodium phosphate buffer (pH 7.0)) in a new tube, thereby obtaining a reaction solution. The resultant reaction solution was incubated at 30° C. for 2 hours, thereby obtaining a reaction product. Thereafter, the fluorescence intensity (hereinafter referred to as "fluorescence intensity A1") of the reaction product in the tube was measured at an excitation wavelength: 360 nm and a fluorescence wavelength: 450 nm. Fluorescence intensity A2 was calculated by subtracting from the fluorescence intensity A1 value the value when the aqueous solution of 0.2 mM 4-MUG alone was added. Fluorescence intensity A was calculated as the average value of fluorescence intensity A2 based on the results of the three measurements.

The S/N ratio in sandwich ELISA was calculated using fluorescence intensity A in the presence of the analyte and fluorescence intensity A in the absence of the analyte, in accordance with Formula (III). "Fluorescence intensity A in the presence of the analyte" was used as the "fluorescence intensity in the presence of the analyte." "Fluorescence intensity A in the absence of the analyte" was used as the "fluorescence intensity in the absence of the analyte."

Comparative Example 4

Except that Fab'-BSA-Bio-DNP was used as the trapping antibody, operations similar to those of Comparative Example 3 were performed to calculate the S/N ratio in sandwich ELISA.

(Results)

Figure 5:
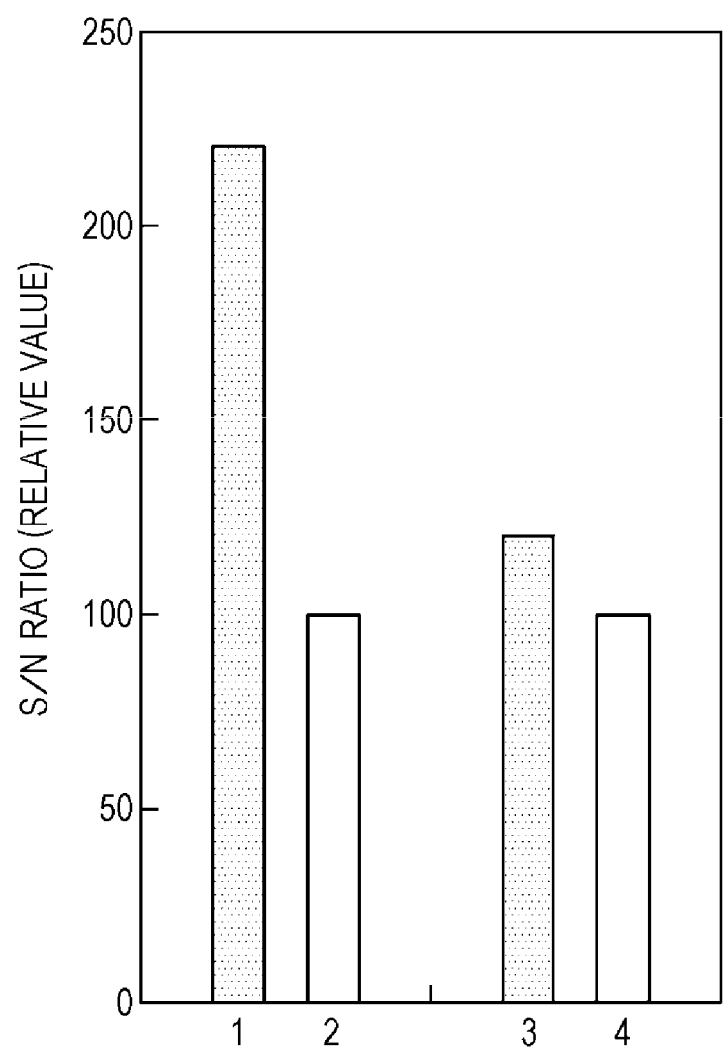
FIG. 5 is a graph showing results of examination of an S/N ratio in Example 2 and Comparative Examples 2 to 4.

FIG. 5 shows results of Example 2 and Comparative Examples 2 to 4. In FIG. 5, Lane 1 represents a relative value of the S/N ratio in Example 2; Lane 2 represents a relative value of the S/N ratio in Comparative Example 2; Lane 3 represents a relative value of the S/N ratio in Comparative Example 3; and Lane 4 represents a relative value of the S/N ratio in Comparative Example 4. In FIG. 5, the relative values of the S/N ratios in Example 2 and Comparative Example 2 are values when the calculated value of the S/N ratio in Comparative Example 2 is defined as 100. In FIG. 5, the relative values of the S/N ratios in Comparative Example 3 and Comparative Example 4 are values when the calculated value of the S/N ratio in Comparative Example 4 is defined as 100.

From the results shown in FIG. 5, in the case of ICT-EIA, the relative value of the S/N ratio in Example 2 was 220. Thus, it was found that ICT-EIA using a trapping antibody containing a linker can improve the S/N ratio more than ICT-EIA using a trapping antibody containing no linker. On the other hand, the relative value of the S/N ratio in Comparative Example 3 was 120. Thus, it was found that ICT-EIA using a trapping antibody containing a linker can improve the S/N ratio more than sandwich ELISA using a trapping antibody containing a linker.

Examples 3 to 5 and Comparative Examples 5 to 7

In order that the amounts of a trapping antibody, a detection antibody and an analyte which are shown in Table 1 were as shown in Table 1, a trapping antibody-containing solution, a detection antibody-containing solution and an analyte-containing solution were mixed in a tube. As the analytes, insulin (manufactured by Acris Antibodies GmbH, trade name: Human Insulin), IL-12/23p40 (manufactured by R&D Systems, trade name: Quantikine Kit Standard), and HBsAg (manufactured by Sysmex Co., trade name: HISCL HBsAg Calibrator) were used. The trapping antibody was prepared as follows. The IgG obtained from the clone shown in Table 1 was fragmented with pepsin, thereby obtaining an F(ab')$_2$ fragment. The resultant F(ab')$_2$ fragment was reduced, thereby obtaining Fab'-SH. BSA-Bio-DNP and a linker (manufactured by Life Technologies, trade name: SM(PEG)$_8$) were reacted with each other, thereby obtaining (PEG)$_8$-BSA-Bio-DNP. BSA-Bio-DNP and EMCS were reacted with each other, thereby obtaining BSA-Bio-DNP-mal.

Fab'-SH and (PEG)$_8$-BSA-Bio-DNP were reacted with each other, thereby obtaining a trapping antibody (Examples 3 to 5). Fab'-SH and BSA-Bio-DNP-mal were reacted with each other, thereby obtaining a trapping antibody (Comparative Examples 5 to 7).

The detection antibody was prepared as follows. In accordance with a conventional technique, the IgG obtained from the clone shown in Table 2 was fragmented with pepsin, thereby obtaining an F(ab')$_2$ fragment. The resultant F(ab')$_2$ fragment was reduced, thereby obtaining Fab'-SH. EMCS was reacted with Gal, thereby obtaining ALP-mal. Fab'-SH and Gal-mal were reacted with each other, thereby obtaining a detection antibody.

TABLE 2

|  |  |  | Clone name | Supply | Amount used |
|---|---|---|---|---|---|
| Example 3 | Trapping antibody | Fab'-(PEG)$_8$-BSA-Bio-DNP | Mouse monoclonal clone #6F7 | Mikuri Immunolab | 300 fmol |
|  | Detection antibody | Fab'-Gal | Mouse monoclonal clone #16E9 | Mikuri Immunolab | 30 fmol |
|  | Test substance | Insulin | — | — | 0 or 0.3 μU |
| Example 4 | Trapping antibody | Fab'-(PEG)$_8$-BSA-Bio-DNP | Mouse monoclonal clone #31052 | R & D Systems | 300 fmol |
|  | Detection antibody | Fab'-Gal | Goat polyclonal AF309 | R & D Systems | 30 fmol |
|  | Test substance | IL-12/23p40 | — | — | 0 or 10 pg |
| Example 5 | Trapping antibody | Fab'-(PEG)$_8$-BSA-Bio-DNP | Mouse monoclonal clone #1053 | Sysmex Co. | 100 fmol |
|  | Detection antibody | Fab'-Gal | Mouse monoclonal clone #85 | Sysmex Co. | 100 fmol |
|  | Test substance | HBsAg | — | — | 0 or 0.025 IU |

TABLE 2-continued

| | | | Clone name | Supply | Amount used |
|---|---|---|---|---|---|
| Comparative Example 5 | Trapping antibody Detection antibody Test substance | Fab'-BSA-Bio-DNP Fab'-Gal Insulin | Mouse monoclonal clone #6F7 Mouse monoclonal clone #16E9 — | Mikuri Immunolab Mikuri Immunolab — | 300 fmol 100 fmol 0 or 0.3 µU |
| Comparative Example 6 | Trapping antibody Detection antibody Test substance | Fab'-BSA-Bio-DNP Fab'-Gal IL-12/23p40 | Mouse monoclonal clone #31052 Goat polyclonal AF309 — | R & D Systems R & D Systems — | 300 fmol 100 fmol 0 or 10 pg |
| Comparative Example 7 | Trapping antibody Detection antibody Test substance | Fab'-BSA-Bio-DNP Fab'-Gal HBsAg | Mouse monoclonal clone #1053 Mouse monoclonal clone #85 — | Sysmex Co. Sysmex Co. — | 100 fmol 100 fmol 0 or 0.025 IU |

Except that the resultant mixture was used, operations similar to those of Example 1, item (1) were performed to form a sandwich complex. Thereafter, operations similar to those of Example 1, items (2) to (4) were performed to recover the streptavidin solid phase. Then, the recovered streptavidin solid phase and 200 µL of an aqueous solution of 0.2 mM 4-MUG were added to 200 µL of buffer B (0.1 M sodium chloride, 0.1 mass % BSA and 0.1 M sodium phosphate buffer (pH 7.0)) in a new tube, thereby obtaining a reaction solution. The resultant reaction solution was incubated at 30° C. for 2 hours, thereby obtaining a reaction product. Thereafter, fluorescence intensity B1 of the reaction product in the tube was measured at an excitation wavelength: 360 nm and a fluorescence wavelength: 450 nm. Fluorescence intensity B2 was calculated by subtracting from the fluorescence intensity B1 value the value when the aqueous solution of 0.2 mM 4-MUG alone was added. Fluorescence intensity B was calculated as the average value of fluorescence intensity B2 based on the results of the three measurements.

The S/N ratio in ICT-EIA was calculated using the fluorescence intensity B in the presence of the analyte and the fluorescence intensity B in the absence of the analyte, in accordance with Formula (III). "Fluorescence intensity B in the presence of the analyte" was used as the "fluorescence intensity in the presence of the analyte." "Fluorescence intensity B in the absence of the analyte" was used as the "fluorescence intensity in the absence of the analyte."

(Results)

Figure 6:
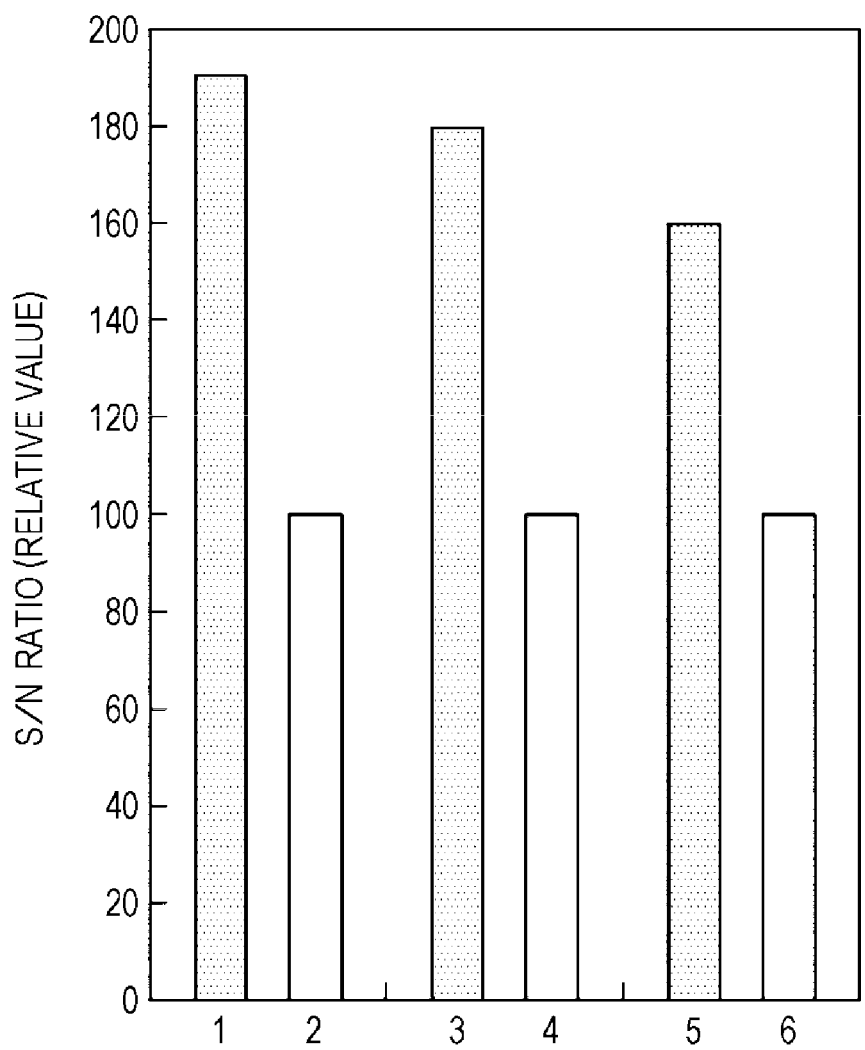
FIG. 6 is a graph showing results of examination of an S/N ratio in Examples 3 to 5 and Comparative Examples 5 to 7.

FIG. 6 shows results of Examples 3 to 5 and Comparative Examples 5 to 7. In FIG. 6, Lane 1 represents a relative value of the S/N ratio in Example 3; Lane 2 represents a relative value of the S/N ratio in Comparative Example 5; Lane 3 represents a relative value of the S/N ratio in Example 4; Lane 4 represents a relative value of the S/N ratio in Comparative Example 6; Lane 5 represents a relative value of the S/N ratio in Example 5; and Lane 6 represents a relative value of the S/N ratio in Comparative Example 7. In FIG. 6, the relative values of the S/N ratios in Example 3 and Comparative Example 5 are values when the calculated value of the S/N ratio in Comparative Example 5 is defined as 100. In FIG. 6, the relative values of the S/N ratios in Example 4 and Comparative Example 6 are values when the calculated value of the S/N ratio in Comparative Example 6 is defined as 100. In FIG. 6, the relative values of the S/N ratios in Example 5 and Comparative Example 7 are values when the calculated value of the S/N ratio in Comparative Example 7 is defined as 100.

From the results shown in FIG. 6, when the analyte was insulin, the relative value of the S/N ratio in Example 3 was 190. When the analyte was IL-12/23p40, the relative value of the S/N ratio in Example 4 was 180. When the analyte was HBsAg, the relative value of the S/N ratio in Example 5 was 160. From these results, it was found that a trapping antibody containing a linker can improve the S/N ratio more than a trapping antibody containing no linker. It was also found that ICT-EIA using a trapping antibody containing a linker can be used to detect various test substances with high sensitivity.

Examples 6 to 8 and Comparative Example 8

Except that a product manufactured by Life Technologies, trade name: EMCS (Comparative Example 8), manufactured by Life Technologies, trade name: SM(PEG)$_2$ (Example 6), manufactured by Life Technologies, trade name: SM(PEG)$_8$ (Example 7) or manufactured by Life Technologies, trade name: SM(PEG)$_{24}$ (Example 8) was used as the trapping antibody, operations similar to those of Example 1 were performed to calculate the complex retention rate.

Figure 7:
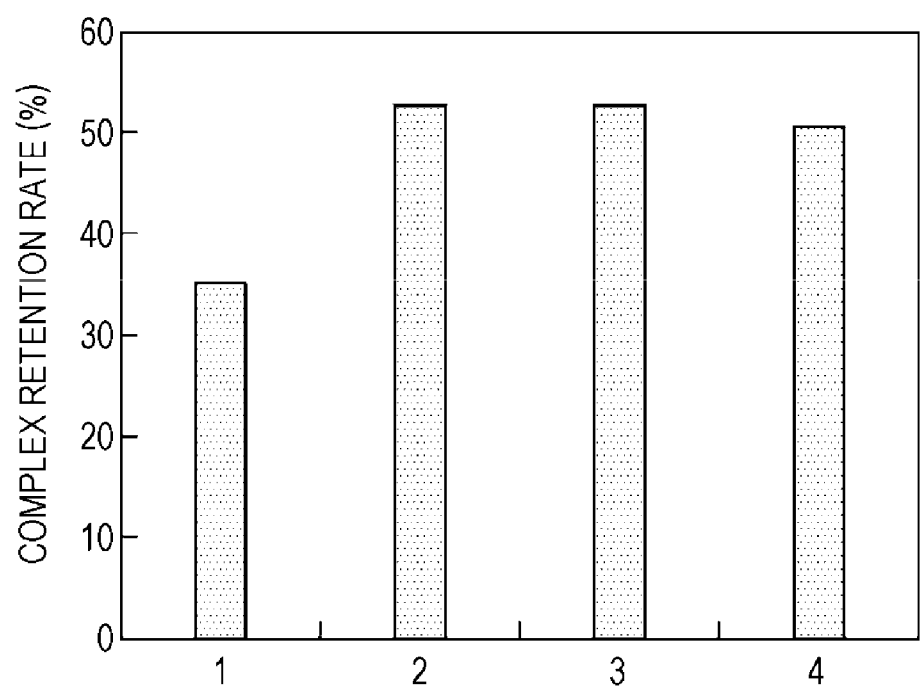
FIG. 7 is a graph showing results of examination of an S/N ratio in Examples 6 to 8 and Comparative Example 8.

FIG. 7 shows results of Examples 6 to 8 and Comparative Example 8. In FIG. 7, Lane 1 represents a complex retention rate in Comparative Example 8; Lane 2 represents a complex retention rate in Example 6; Lane 3 represents a complex retention rate in Example 7; and Lane 4 represents a complex retention rate in Example 8.

From the results shown in FIG. 7, the complex retention rates in Example 6 to 8 were higher than that in Comparative Example 8. From these results, it was found that trapping antibodies containing various PEG linkers different in addition molar number of the oxyalkylene groups can improve the complex retention rate.

As explained above, it was found that a trapping body containing a binding substance, a support and a linker which links the binding substance and the support with each other can suppress the dissociation of an immune complex (namely, sandwich complex) and improve the S/N ratio in ICT-EIA.

What is claimed is:
1. A method for detecting an analyte in a sample, comprising the steps of:
 (A) forming a first complex comprising:
 an analyte;
 a first antibody fragment which specifically binds to the analyte, wherein said first antibody fragment is a Fab or Fab';
 a second antibody fragment which specifically binds to a site of the analyte, the site being different from a site to which the first antibody fragment specifically binds, wherein said second antibody fragment is a Fab or Fab', and wherein said second antibody fragment is conjugated through a linker to a support that comprises a dinitrophenyl group and a biotin, wherein the support is bovine serum albumin (BSA); and
 an anti-dinitrophenyl antibody solid phase;
 (B) separating a sandwich complex comprising the analyte, the first antibody fragment, and the second anti- body fragment conjugated through the linker to the support, from the anti-dinitrophenyl antibody solid phase;
(C) allowing an avidin solid phase or a streptavidin solid phase to trap the sandwich complex to form a second complex; and
(D) detecting the analyte of the second complex,
wherein the linker is a polyethylene glycol chain, and wherein said polyethylene glycol chain has between 2 and 24 oxyethylene groups on average.

2. The method according to claim 1, wherein said sandwich complex is separated from said anti-dinitrophenyl antibody solid phase by a separation reagent in step (B).

3. The method according to claim 2, wherein said separation reagent is a dinitrophenyl amino acid.

4. The method according to claim 1, wherein
the first antibody fragment has a labeling substance, and
a signal based on the labeling substance comprised in the second complex is detected in the step (D).

5. The method according to claim 4, wherein the labeling substance is at least one selected from the group consisting of an enzyme, a fluorescent substance and a radioactive substance.

6. The method according to claim 4, wherein the labeling substance is β-galactosidase or alkaline phosphatase.

7. The method according to claim 4, wherein the signal is luminescence, fluorescence or color development.

* * * * *